United States Patent
Mahon et al.

(10) Patent No.: US 8,998,889 B2
(45) Date of Patent: Apr. 7, 2015

(54) SYSTEM AND METHOD FOR CONTROL AND MONITORING OF CONFORMAL THERMAL THERAPY

(71) Applicant: Profound Medical Inc, Toronto (CA)

(72) Inventors: Cameron Mahon, Georgetown (CA); Mathieu Burtnyk, Toronto (CA)

(73) Assignee: Profound Medical, Inc., Toronto, ON (*) Notice: Subject to any disclaimer, the term of this patent is extended or adjusted under 35 U.S.C. 154(b) by 286 days.

(21) Appl. No.: 13/627,029

(22) Filed: Sep. 26, 2012

(65) Prior Publication Data

US 2013/0158577 A1 Jun. 20, 2013

Related U.S. Application Data

(60) Provisional application No. 61/538,982, filed on Sep. 26, 2011.

(51) Int. Cl.
| | |
|---|---|
| *A61B 18/04* | (2006.01) |
| *A61N 7/02* | (2006.01) |
| *A61B 17/00* | (2006.01) |
| *A61B 18/00* | (2006.01) |
| *A61B 19/00* | (2006.01) |
| *A61N 7/00* | (2006.01) |

(52) U.S. Cl.
CPC ........ *A61N 7/02* (2013.01); *A61N 7/022* (2013.01); *A61B 2017/00119* (2013.01); *A61B 2018/00791* (2013.01); *A61B 2019/5236* (2013.01); *A61N 2007/0095* (2013.01)

(58) Field of Classification Search
CPC ........... A61B 2017/00119; A61B 2018/00791; A61B 2019/5236; A61B 18/1492; A61N 2007/0095; A61N 7/02; A61N 7/022
USPC .......................................................... 606/27
See application file for complete search history.

(56) References Cited

U.S. PATENT DOCUMENTS

| | | | |
|---|---|---|---|
| 6,254,553 B1 | 7/2001 | Lidgren et al. | |
| 6,589,174 B1 | 7/2003 | Chopra et al. | |
| 7,044,960 B2 * | 5/2006 | Voorhees et al. | 607/96 |
| 7,771,418 B2 * | 8/2010 | Chopra et al. | 606/28 |
| 2003/0004439 A1 | 1/2003 | Pant et al. | |
| 2006/0206105 A1 | 9/2006 | Chopra et al. | |
| 2007/0239062 A1 | 10/2007 | Chopra et al. | |
| 2011/0034833 A1 | 2/2011 | Chopra et al. | |
| 2011/0144524 A1 | 6/2011 | Fish et al. | |

FOREIGN PATENT DOCUMENTS

WO 2013098690 7/2013

OTHER PUBLICATIONS

D. Arora, M. Skilliar & R. B. Roemar, "Model-Predictive Control of Hyperthermia Treatments", IEEE Transactions on Biomedical Engineering, Jul. 2002, p. 629-39, vol. 49, No. 7.

Y. Feng & D. Fuentes, "Model-based planning and real-time predictive control for laser-induced thermal therapy", Int. F. Hyperthermia, Dec. 2011, p. 751-61, vol. 27, No. 8.

* cited by examiner

*Primary Examiner* — George Manuel

(74) *Attorney, Agent, or Firm* — Intrinsic Law Corp.; Ibrahim M. Hallaj

(57) ABSTRACT

A system and method are disclosed for thermal therapy that takes into account predictive calculations of tissue temperature, and can be used to control the operation of a conformal thermal therapy procedure and device. In some embodiments, the tissue ablation area is part or all of a prostate gland. The method includes, in preferred embodiments, simulations and or calculations of future temperatures based on some or all of the following information: current temperatures, heat diffusion in the tissue, blood perfusion in the tissue, and planned ultrasound energy depositions. The calculated temperature maps can be used to design, control, or terminate the therapy.

18 Claims, 13 Drawing Sheets time = t1

SYSTEM AND METHOD FOR CONTROL AND MONITORING OF CONFORMAL THERMAL THERAPY

RELATED APPLICATIONS

This application claims the benefit and priority of U.S. Provisional Application 61/538,982, entitled "System and Method for Control and Monitoring of Ultrasound Thermal Therapy," filed on Sep. 26, 2011, which is hereby incorporated by reference.

TECHNICAL FIELD

The present application relates to ultrasound therapy systems, and particularly to the operation of an array of ultrasound sources for use in such systems. More specifically, the present system and method is directed to control and monitoring of conformal thermal therapy procedures using active ultrasonic heating elements placed in a region of diseased tissue.

BACKGROUND

Ultrasonic transducers have been employed in ultrasound therapy systems to achieve therapeutic heating of diseased and other tissues. Arrays of ultrasound transducers operating to form a beam of ultrasonic energy cause a conversion of sound to thermal energy in the affected tissue areas or treatment volumes, and a subsequent beneficial rise in the temperature in the treatment volumes.

In image-guided ultrasound therapy systems, a patient and the ultrasound therapy apparatus are generally disposed in an imaging volume such as a magnetic resonance imaging (MRI) apparatus, which allows guidance of the applicator placement, and in addition allows monitoring of the treatment effect on the tissue by providing real-time data from which temperature maps can be calculated. A clinical operator can then monitor the progress of the therapy within the treatment volume or diseased tissue and manual or automated changes can be made to the ultrasound power signals based on input from the results and progress of the treatment. With proper monitoring of the heating effect, ultrasound therapy systems can be used to treat harmful cells and to controllably destroy tumors.

The temperature created by the absorption of sound in a sound-conducting medium is not uniform. When the acoustic field is not generally focused, the temperature rise is highest close to the source of sound and it decreases with distance from the source. The sound created by a piston-shaped transducer is highly directional. As such there will be an increase in temperature along the line perpendicular to the center of the face of the piston with only small increases in temperature in the volumes adjacent to that perpendicular line. The resultant shape of thermal energy deposition is similar to the flame from a match with a narrow tip and being slightly wider at the base.

In any material, local temperature differences gradually disappear due to heat transfer from areas of high temperature to areas of lower temperature. In live tissue thermal diffusion and blood circulation are two of the main mechanisms by which heat transfer take place. If there is an area of increased temperature in tissue, these heat transfer phenomena work to reduce the peak temperature and increase the surrounding tissue temperature.

Work has been done to demonstrate the use of magnetic resonance imaging (MRI) guided transurethral ultrasound therapy systems for treatment of disease such as prostate cancer in men. See, e.g., Chopra, et al., "MRI-compatible transurethral ultrasound system for the treatment of localized prostate cancer using rotational control," Med Phys 35(4): 1346-1357, 2008. Also see, U.S. Pub. 2007/0239062; U.S. Pat. No. 6,589,174 "Technique and apparatus for ultrasound therapy," 2003; U.S. Pat. No. 7,771,418 "Treatment of diseased tissue using controlled ultrasonic heating," 2010. Such systems, including cumulative published and patented work by or for the present applicant, all of which are hereby incorporated by reference, teach the use of transurethral ultrasonic energy to the diseased prostate to reach a desired target temperature in the diseased tissue to achieve the clinical result, which is usually the necrosis of the diseased tissue cells in the prostate. MRI guidance and temperature monitoring of the treatment in realtime enables control of the power to the ultrasound therapy transducers as well as control of the rotation of an array of such transducers disposed axially along an elongated applicator inserted into the patient's urethra in the vicinity of the diseased prostate.

It is understood that it is necessary to control the operation of such systems in use, as uncontrolled, or poorly controlled, operations can lead to unwanted injury to the patient through overheating the patient's tissue or applying the heat treatment to organs and tissues that should not be treated. See, e.g., U.S. Pub. 2007/0239062 "Method and apparatus for obtaining quantitative temperature measurements in prostate and other tissue undergoing thermal therapy treatment," 2007; U.S. Pub. 2006/0206105 "Treatment of diseased tissue using controlled ultrasonic heating," 2006.

One concern relates to the obvious harm of unwanted cell death from overheating healthy or critical organ tissue in the context of prostate treatment. Another concern relates to acoustic factors that can degrade or impede the operation of the therapy system if tissue proximal to the therapy system operated in a way that causes boiling (approximately 100 Celsius) or cavitation (formation of gas voids in the tissue) in the tissue. These effects may be beneficial or desired in some contexts, addressed elsewhere, but for the present purpose, unless stated otherwise, the preferred embodiments below rely on temperature control rather than mechanical, boiling, cavitation or other effects to achieve their desired result. These concerns are recognized but not suitably or perfectly solved for all situations in the presently-cited and similar references in the field.

Still other work has been published describing the real and simulated effects of ultrasound thermal therapy systems. See, e.g., Burtnyk et al., "Quantitative analysis of 3-D conformal MRI-guided transurethral ultrasound therapy of the prostate: theoretical simulations," Int J Hyperthermia 25(2): 116-131, 2009; Burtnyk et al., "Simulation study on the heating of the surrounding anatomy during transurethral prostate therapy: A 3-D theoretical analysis of patient safety," Med Phys 37(6): 2862-2875, 2010. Again, the above and similar efforts indicate a recognition of the need to control, measure, predict and otherwise understand the effects of conformal thermal therapy systems.

Yet another aspect of conformal thermal therapy treatment is that of time-dependence and the three-dimensional nature of heat conduction and diffusion. If a thermal treatment leads to a certain temperature next to a target boundary in the treatment zone, it is possible for the target temperature at the target boundary to be exceeded by heat transfer from an adjacent area with higher temperature.

The present disclosure and inventions address, among other aspects, the above issues and cover systems and methods for better thermal treatment in patients suffering from disease such as prostate cancer.

SUMMARY

Embodiments hereof are directed to systems and methods for improving the outcome of ultrasound ablation in patients. In some respects, the present disclosure provides a method of predicting the temperature of tissue affected by the ultrasound beam and heat transfer within the tissue, and using the prediction to control the treatment and the parameters of the ablation.

Some embodiments are directed to ultrasound ablation in the prostate gland using an elongated ultrasound therapy device inserted into the urethra of a patient. The device typically includes a plurality of ultrasonic elements disposed within said elongated portion. Once the device has been inserted, it can be programmably rotated within the urethra and deliver ultrasonic energy of variable intensity into the prostate.

In some aspects, the present method and system improve the performance of ultrasound ablative treatment by tackling the potential problem of treating certain difficult axial shapes of treatment volume. In one embodiment simulations of thermal diffusion and/or perfusion around treated tissue are used in real time to determine whether treatment should continue. In another embodiment, such heat transfer calculations are combined with predictions of ultrasonic heat deposition in order to make this decision. In a further embodiment, these calculations can be utilized for making decisions about how to proceed with therapy, for example but not limited to, what settings to use for power and rotation angle in the treatment.

Still other aspects are directed to conformal thermal therapy of diseased target volumes where the energy source device is located outside the target volumes as is done in FUS and HIFU therapies. The time-predictive features below will enable more precise and safer thermal treatments in these applications.

The aforementioned calculations and simulations can also be used in the treatment planning stage before ultrasound therapy commences.

BRIEF DESCRIPTION OF THE DRAWINGS

For a fuller understanding of the nature and advantages of the present invention, reference is made to the following detailed description of preferred embodiments and in connection with the accompanying drawings, in which.

DETAILED DESCRIPTION

As discussed above, better ultrasound thermal therapy applicators can improve treatment of diseases such as tumors, and for example as used in trans-urethral treatment of prostate cancers in male patients.

Traditional treatment using ultrasound thermal therapy typically employs one or more temperature control points along the target boundary as discussed in some of the references listed above. Safer and more effective treatments are enabled using the present system and method. Since temperature at the control points will increase due to the deposited/absorbed energy of the ultrasound, care must be exercised to not exceed a maximum temperature and/or thermal dose within healthy tissues or organs proximal to the location to which the thermal therapy is being applied. Nerve and vascular and other healthy organs and tissues can become damaged if the thermal therapy is applied at either the wrong locations or if the therapy exceeds a safe energy level or duration. The determination of the appropriate energy levels and other parameters for the therapy are the subject of studies and surgical planning processes, which are sometimes aided by computer simulations so as to approximate a therapy routine before subjecting a patient thereto.

Figure 1:
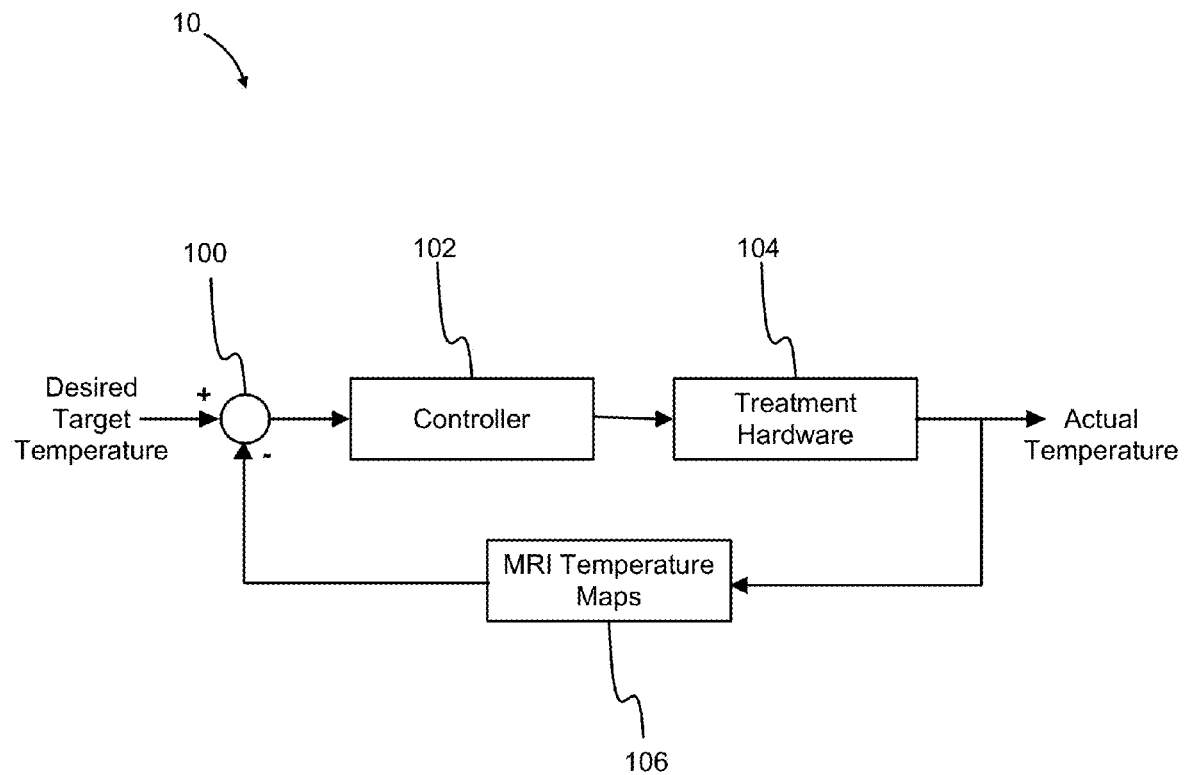
FIG. 1 illustrates a control scheme for an image guided thermal therapy process.

FIG. 1 illustrates a basic control method 10 for obtaining a desired temperature at a control point in a region of interest undergoing thermal therapy treatment. A desired target temperature is input into the therapy system or process, which can include hardware, executable instructions, program code and stored data. A controller 102 is used to generate control signals according to the desired target temperature and deliver the control signals to treatment hardware 104. The output of the treatment hardware 104 affects the actual temperature at the control point, which is generally a function of time. That is, the actual temperature is generally influenced by the action of the treatment hardware 104 and changes in time. As mentioned, MRI thermometry is used to generate temperature maps 106, substantially in realtime according to some embodiments, though a delay for imaging and processing is allowable. The mapping of the MRI imaging to temperature maps 106 is fed back into the loop 100 so as to inform controller 102 and adjust the control signals to treatment hardware 104 in the subsequent steps of the treatment. This general method 10 is followed until the treatment's goals are satisfied (e.g., a given temperature is reached in the treatment region) or an alarm or other action interrupts the process.

Figure 2:
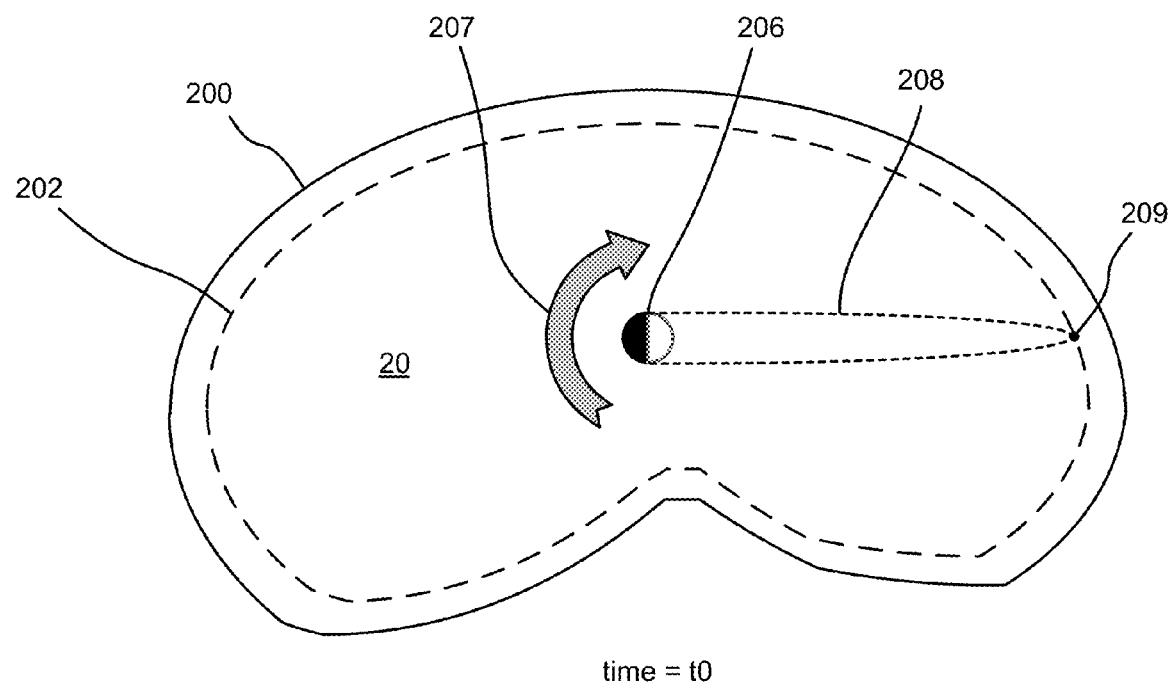
FIG. 2 illustrates a snapshot of the active heating of a target volume at time t=t0.

FIG. 2 illustrates a cross section of a prostate 20 undergoing thermal therapy and shown at some instant in time t0. The prostate 20 has an organ boundary 200. The therapy can be prescribed to be applied to a portion of the prostate 20 or to the entirety of the prostate 20. In some embodiments, to avoid unwanted heating outside the prostate, a treatment boundary may be defined, for example in a treatment planning step prior to or during application of the thermal therapy treatment. In an embodiment, a treatment zone is define to be that substantially within a general treatment target boundary 202 outlining a sub-region of the entirety of prostate 20. This treatment volume, zone or region boundary 202 may be drawn by an operator using a user interface to the image guided therapy system and software. The target boundary 202 may alternatively be computed automatically using computer software and algorithms for detection of the diseased region and calculation of a safe sub-region requiring thermal therapy. A combination of human and machine detection and determination of the treatment target boundary 202 is also possible. In other embodiments, thermal treatment may target substantially the entire volume of the patient's prostate.

As mentioned herein and in related references, an elongated transurethral prostate therapy applicator 206 is inserted longitudinally into the patient's prostate and into a space within the prostate 20 so as to perform conformal thermal therapy using the applicator. As described, the thermal therapy applicator is rotated about its axis using a computer-controlled motor as described in earlier patents and applications, including: U.S. Pat. Nos. 6,589,174; 7,771,418; U.S. Pubs. 2007/0239062; 2011/0034833; U.S. patent application Ser. Nos. 12/932,914; 12/932,923; 12/932,920; and 13/065,106, which are all hereby incorporated by reference.

As represented in the figure, and according to certain designs of applicator 206, the thermal therapy (e.g., ultrasound energy) is directionally emitted from an active face of applicator 206. Here, a flame-shaped profile or zone 208 represents the general emission (and deposition) of energy into the prostate tissue at a given moment during the treatment. During treatment, ultrasonic energy is transmitted from the active face of the transducer elements of applicator 206 into the diseased tissue proximal to and in the path of the heating zone 208. The extent to which heating profile 208 extends into the patient depends on a number of physical factors including: the power applied to the transducer elements of applicator 206, the composition of the intervening tissue of prostate 20 such as its thermal conductivity, the operating frequencies of the transducer element, perfusion (cooling by heat removal through vascular blood flow), non-linear effects, and other factors. The heating in lobe 208 tapers off near the edges of treatment lobe 208, and as such, this zone is defined by the manner in which the user chooses to measure it. But in any case, it is generally shaped and extends according to the factors given above. Therefore, a general depth or radius of thermal treatment can be described or quantified, which may be time-dependent as explained further below.

Therefore, the extent of the treatment radius or length of treatment zone 208 defines a control point 209 associated with the intersection of treatment zone 208 and the target boundary 202 of the volume undergoing treatment. This can be described in terms of the distance from the center of applicator 206 which is clinically affected by the applied heating energy of the applicator device.

The therapy applicator 206 is made to rotate about its central axis so as to sweep through the desired treatment volume defined by a treatment boundary 202. The rotation 207 is performed at a predetermined, calculated, planned, or dynamic rotation rate during the therapy process. In the shown example, the applicator 206 rotates in a clockwise direction 207 as seen in this cross sectional slice. Therefore the direction of the treatment zone lobe 208 and control point 209 at any given moment would depend on the angular position of applicator 206. The patient and prostate 20 are spatially at rest or fixed in the laboratory/clinical frame of reference. The slower the rate of rotation 207, the longer the applicator's active surface dwells at or around an angular position and the greater the accumulated thermal dose and heating of the target tissue along zone 208 and at control point 209.

Figure 3:
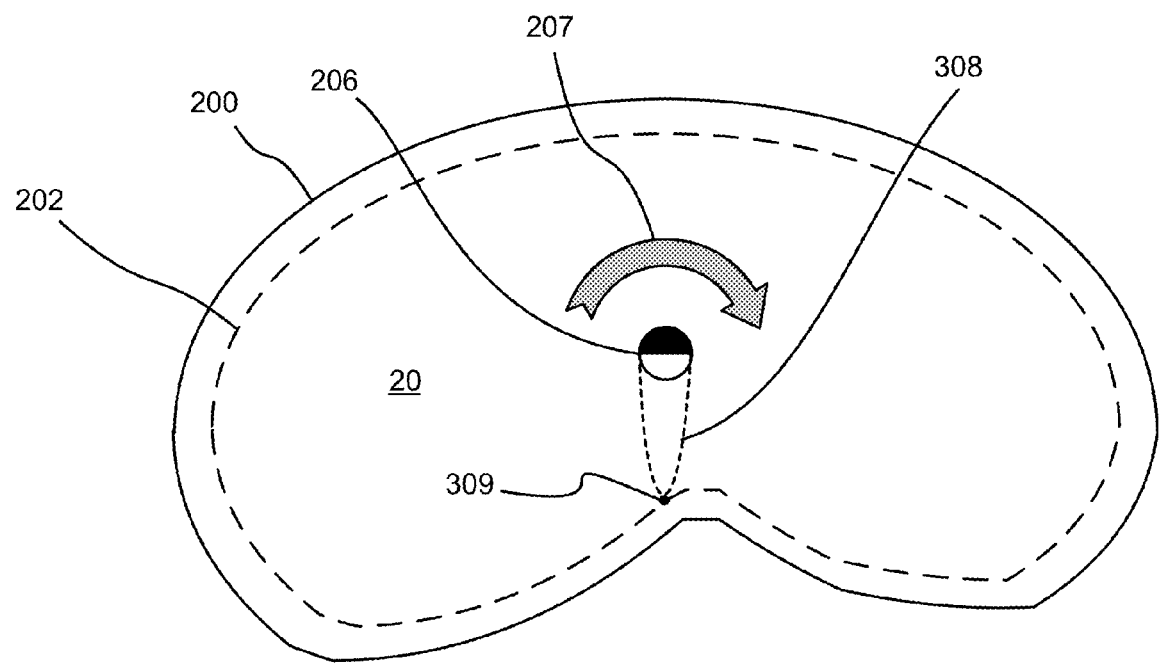
FIG. 3 illustrates another snapshot, sometime after that of the previous figure, at t=t1.

FIG. 3 illustrates a progression of the prostate treatment of the previous figure at a somewhat later time t1. Continuing its clockwise rotation about its axis, applicator 206 has progressed at t1 to a new angular position (discretely or continuously) so that at the snapshot illustrated its active heating energy lobe 308 is applied downwards as shown and in a direction where the prostate 20 is relatively small in extent. Comparing FIGS. 2 and 3 one observes that the extent or length of the heating lobes (209, 309) has been adjusted as necessary, dynamically, so as to avoid exceeding the thermal thresholds outside the treatment target boundary 202. In other words, as the target boundary's distance from the center of the applicator 206 varies (in time and angular position) the system adjusts the heating output of the applicator 206 so its therapeutic effects are substantially confined to the desired volume within treatment target boundary 202. Those skilled in the art would appreciate that the present system relies on heat conduction and diffusion, and would understand the maximum achievable temperature gradients in such a context. It has been understood from histological studies, what tissue types are capable of surviving various temperature elevations, and an acceptable thermal therapy plan can be prescribed in most or all cases so that the diseased tissue is treated and the healthy or critical adjacent tissue survives the treatment. Therefore, as explained above, practitioners and system designers will apply segmentation and control techniques so as to optimally treat the tissues within the target boundary 202 while substantially not damaging tissues outside but proximal to boundary 202. Also, the power and rate of rotation of the active transducers of applicator 206 are modulated and controlled to conformally provide the desired amount of heat output and treatment lobe sizes 208, 308 as a function of time and angular location within prostate 20.

The above nature of the present treatment method and system can therefore benefit from the best controls that can be applied to them. In this disclosure, some aspects are directed to such controls and computational tools to best account for the dynamic nature of the problem being solved. The inventors appreciate that the applied heat and resulting temperature rise at each location and each slice in the 3D treatment volume are time-dependent. For example, it is recognized how to handle situations where the heating and temperature rise at some location are affected by previous instants in time, and that present heating will affect future conditions along the treatment path and in neighboring spatial locations.

To achieve the present results, the inventors utilize among other things, the ability to non-invasively measure temperature at frequent intervals within the patient's anatomy. As described herein and in related applications, imaging thermometry, e.g., using MRI images obtained in real time or substantially in real time are used to monitor the progress of the thermal therapy. A succession of such MRI thermal maps is obtained at each cross section of the prostate undergoing therapy. It is not critical that the slice thicknesses of the therapy and the thermometry components of the system be the same. Interpolation, curve fitting and other techniques can be used to smooth out, over-sample, under-sample or otherwise account for any differences in such spatial or temporal resolution.

In an aspect, the thermometry temperature measuring scans are taken as data that is input into a calculation engine. This temperature map data is operated on and supplemented with calculated thermal predictions. In one or more embodiments, each thermal image will be processed using a predictive thermal diffusion-perfusion method. Software allowing computer simulations of the temperature dispersion in a region of interest is incorporated into the therapy system. As discussed in more detail below, relevant factors including the measured temperature profiles are used to guide and adjust the progress of a thermal therapy treatment. The capabilities of the system include spatial and temporal interpolation, extrapolation, fitting, and algorithmic computations using bioheat transfer relationships that apply to the prostate organ during treatment. Therefore, the system avoids unwanted temperature overshoots and permits maximal use of safety zones incorporating such predictive knowledge to obtain the most efficient and fastest conformal thermal therapy treatments within the organ. This is applied either on a slice-by-slice basis in two dimensions (2D) or across multiple slices in three dimensions (3D).

Figure 4:
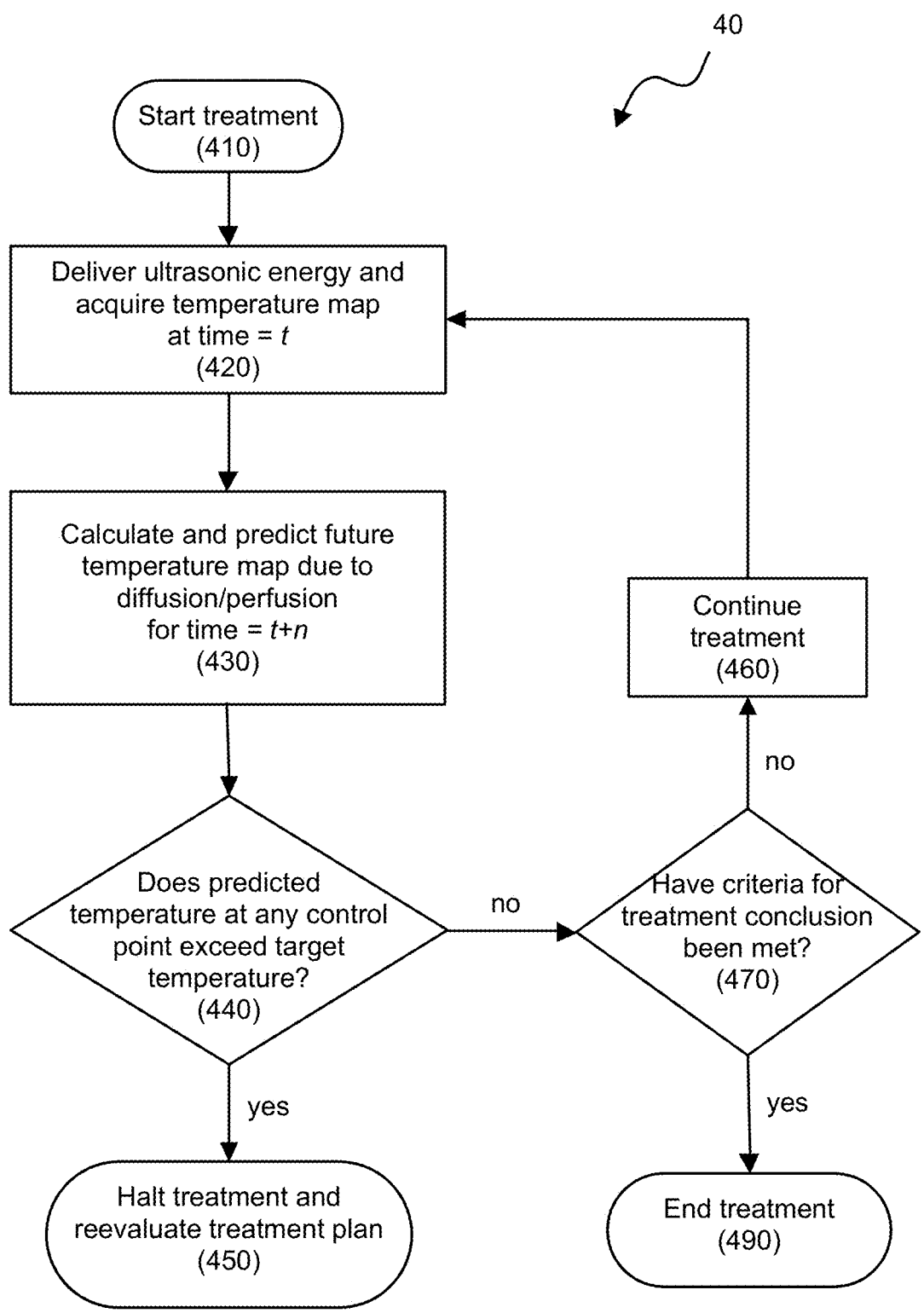
FIG. 4 shows a flowchart of one embodiment of the invention, in which treatment is halted and the treatment plan reevaluated if the temperature is predicted to exceed the target temperature at the control point due to heat transfer.

FIG. 4 illustrates an exemplary logic flow diagram in a method 40 for applying thermal therapy under image guidance. Upon commencement of the start of treatment 410, ultrasonic energy is delivered at time t and step 420. A temperature map is acquired using MRI temperature mapping in a MRI imaging system during this step. A future temperature map accounting for dynamic thermal behavior in the tissue under treatment is calculated at step 430. The calculation or simulation of the future temperature may include physical phenomena such as conduction, diffusion, perfusion, nonlinear effects, and so on. The expected progress of the target temperature isotherm at time t+n, where n can be any time interval (e.g., one second increments or an interval related to the frequency of acquisition of imagery in an image guidance system), is calculated or simulated as described below in an example.

The calculated or simulated future temperature from step 430 is compared against the target boundary temperature at step 440. If the thermal inertia as determined from the future temperature computation and prediction will cause the maximal target isotherm to cross the target boundary 202 then a special output may be generated. The special output may be a signal to cause a stopping or reducing of the rate of therapy. This can be achieved by reducing or shutting off the driving signals (power) to one or more transducer elements in applicator 206, at step 450. This process is described with respect to an exemplary embodiment of course and other implementations are reasonable and would be apparent to one skilled in the art upon reviewing this description. In an embodiment, this can also result in stoppage of the rotation (mechanical movement) of the applicator 206 within the patient, as the movement is driven by a controllable electrical-mechanical prime mover. In some embodiments, prediction that the temperature excursion will spread beyond the target boundary 202 results in an audible and/or visible alarm being raised, and in yet other embodiments, a portion of the target boundary 202 that is going to be breeched will be highlighted on a graphical interface. Otherwise, if no unwanted temperature excursions are predicted, and the requirements for concluding the treatment have not been met (470) the treatment will continue as planned (460). If the treatment goals are achieved in 470 the treatment method is terminated at 490. Feedback and output to the operator of the system or to a log of the system's activity can be recorded and kept in the patient's medical record, a secure storage data repository, on an operator's work station console, transmitted to another device or computer, and so on. Maximal and minimal values of the controlled parameters may be defined and a ceiling or floor value of such parameters can be enforced.

Figure 5:
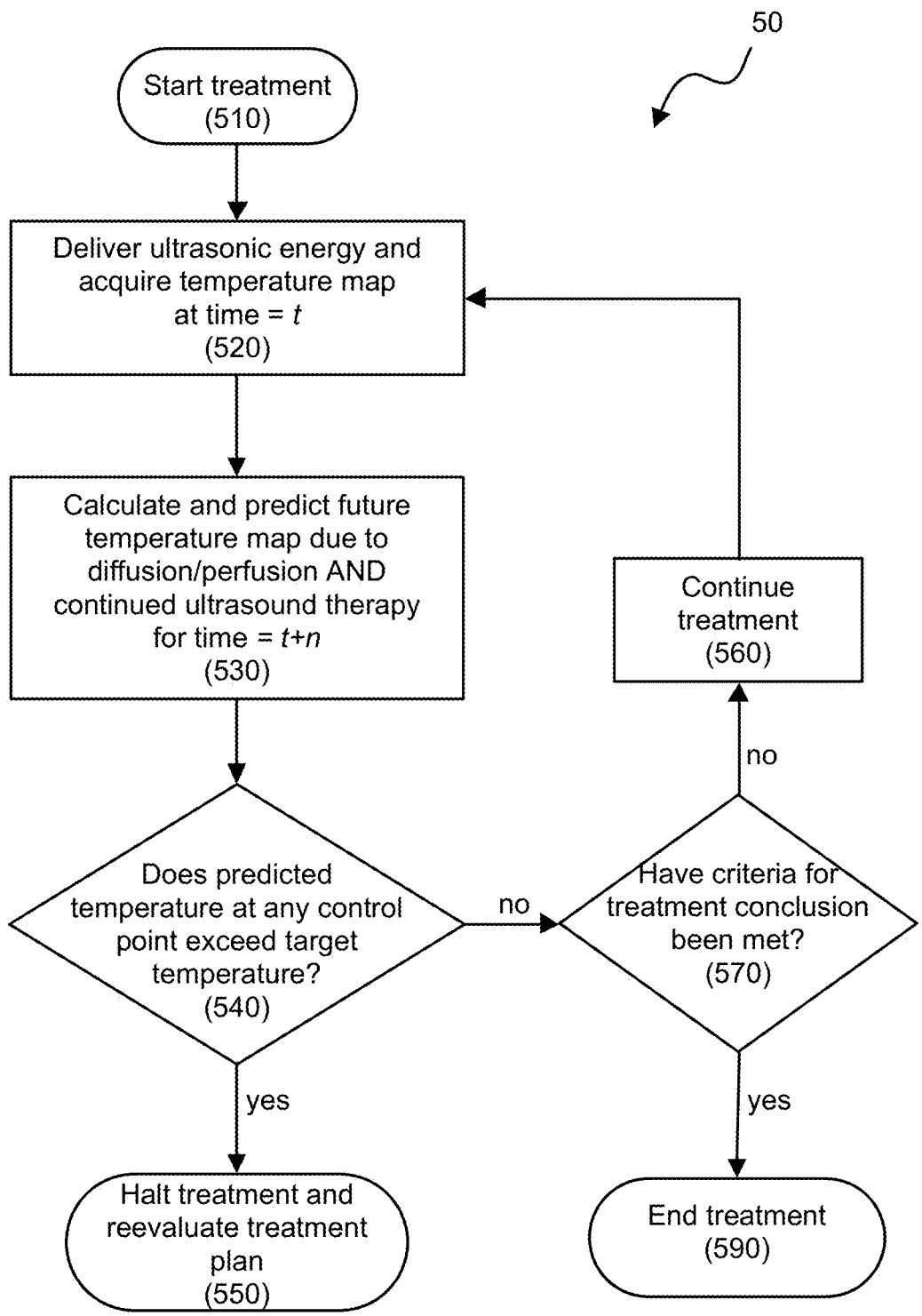
FIG. 5 shows a flowchart of another embodiment in which treatment is halted and the treatment plan is reevaluated if a combination of the heat transfer calculations and predictions of the next energy deposition step would cause the target temperature to be exceeded.

In another embodiment 50 is depicted in a flowchart shown in FIG. 5. A difference is that the progression of the ultrasound energy deposition will be predicted and added to the predicted thermal diffusion-perfusion map at 530. This may provide a useful prediction of the possibility of target boundary breech in some embodiments.

Several techniques for computing the thermal effects in a system such as described can be appreciated by those skilled in the art. The present disclosure is meant to apply generally to these types of bioheat transfer equations, and the examples below are not provided by way of limitation. So other physical effects can be modeled by suitable terms, some of which are described in the literature known to those skilled in the art and the publications mentioned herein, which are incorporated by reference for this purpose. For example, a thermal heat diffusion calculation can be based on a bioheat transfer equation, e.g.:

$$\rho c_t \frac{\partial T}{\partial t} = \nabla \cdot (k_t \nabla T) - w_b c_b (T - T_b) + Q$$

where $\rho$ is tissue density; $c_t$ is tissue specific heat; $k_t$ is thermal conductivity; $w_b$ is blood perfusion; $c_b$ is the blood specific heat; $T_b$ is the blood temperature; T is the tissue temperature; and Q is the ultrasound heat deposition.

Figure 6:
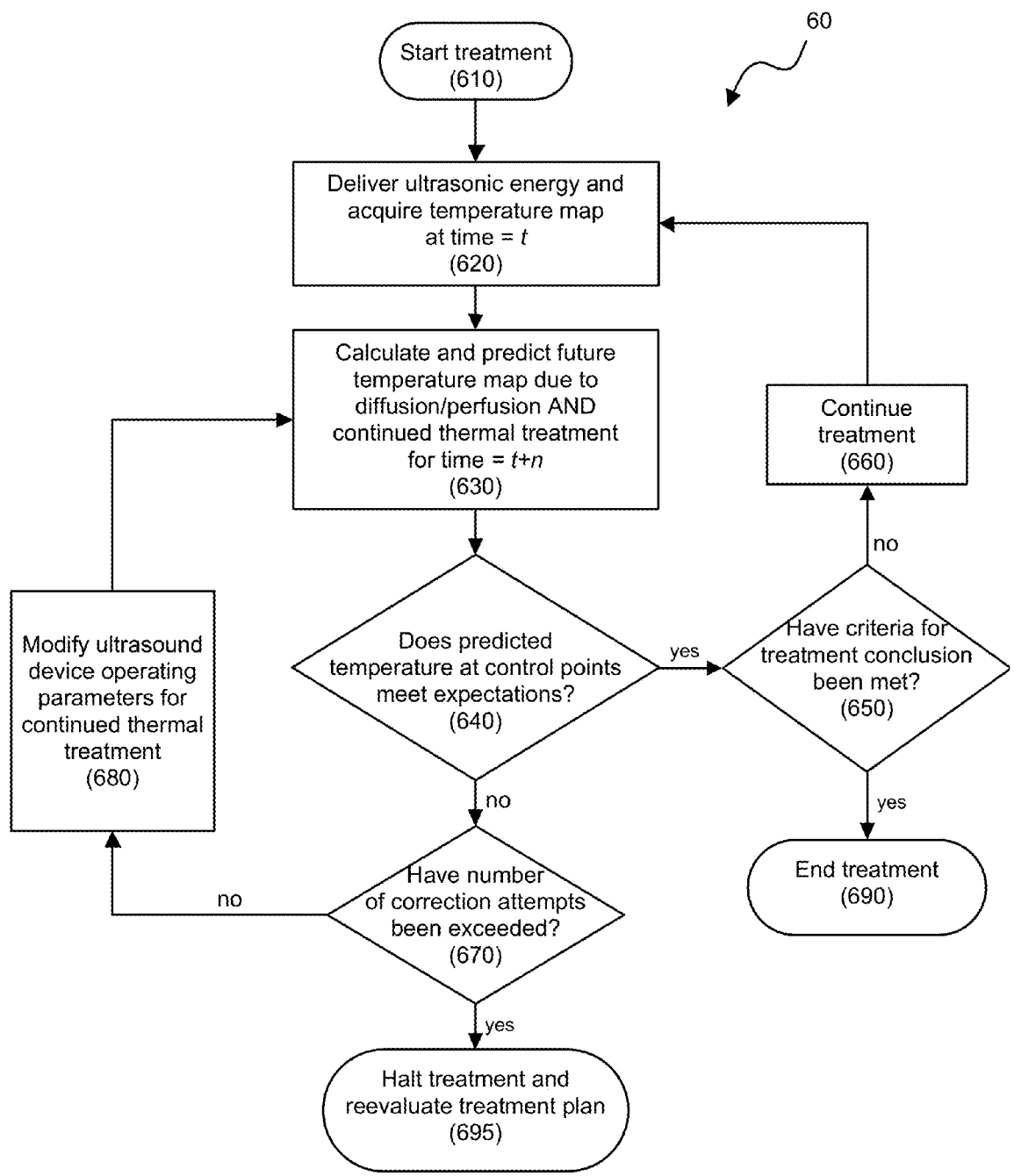
FIG. 6 shows a flowchart of a further embodiment in which parameters of the next ultrasonic energy emission, such as rotation rate and amplitude, are modified according to predictive calculations that incorporate heat transfer and the effect of said energy deposition.

FIG. 6 illustrates an exemplary treatment method 60 including a substantially real-time feed forward predictive control to the energy output of the therapy applicator 206. The operation of the therapy proceeds as described in FIG. 5, except that if calculations show that the target temperature will be exceeded, the treatment need not necessarily be halted. Instead, ultrasound device operating parameters may be modified and the predicted temperature map may be recalculated. If recalculation of the temperature map once more results in unwanted temperatures, the control parameters may be modified in a different way. The operator will determine the number of attempts made to modify the device control parameters in order to obtain a permissible temperature map, before the treatment is halted and the treatment plan reevaluated.

The control method can include changing the direction of rotation in areas of rapidly changing radius so that there is little risk of overshoot. Since this treatment happens on several slices at the same time, there is the potential for one slice to require treatment in one direction while another slice requires treatment in the opposite direction. If this is the case then a value judgment will have to be made balancing the benefits of speed and safety.

The illustrated logic flow diagrams are merely exemplary in that many other steps may be performed in addition to those shown. Also, other steps may be substituted for the shown steps, and the ordering of the steps may be accomplished in any way necessary to achieve a given outcome in certain situations. The steps described can be implemented using a combination of electronic circuitry, e.g., processors, and software instructions that run on those processors. The software instructions may be coded and stored on a machine readable medium such as a digital memory device coupled to a computing device or networks with access by the processors.

In some embodiments, a database of information may be generated by tracking the results of one or more therapy procedures so as to obtain useful predictive results that can be applied to future treatments.

A control system and method is therefore described. In various embodiments, the system and method includes modules and components that can include hardware and software and information and signals. Inputs are processed and outputs are generated to enable the operation of the system and method.

Exemplary inputs usable in the present invention include: treatment planning information, such as geometric information describing a patient's prostate shape and location, tissue characteristics of the patient or the target zone, the desired treatment target boundary, the relative positioning of the patient's urethra, etc.; temperature information, such as the temperature of one or more control points (e.g., one control point along the treatment boundary at each 2D slice along the active length of the elongated treatment applicator), target temperatures, treatment radius, maximal acceptable temperatures, temperature differences between an actual, calculated or desired temperature; applicator information, such as identification of active elements, the relative positions of the elements, the size of the elements, and whether the elements are powered.

Exemplary controls include: power gain coefficients (Kp); angular (Omega) gain coefficients (Kw); minimum and maximum tuning radius; algorithms for calculating needed power and rotation rates; states of each element or status of the applicator device as a whole; frequency or range of useful frequencies; and updating of the states of the elements and applicator. These aspects are further described below.

Exemplary outputs available from the present invention include: power and frequency of the driving signals applied to the applicator and its active elements; and the rate of rotation of the applicator about its central axis.

Figure 7:
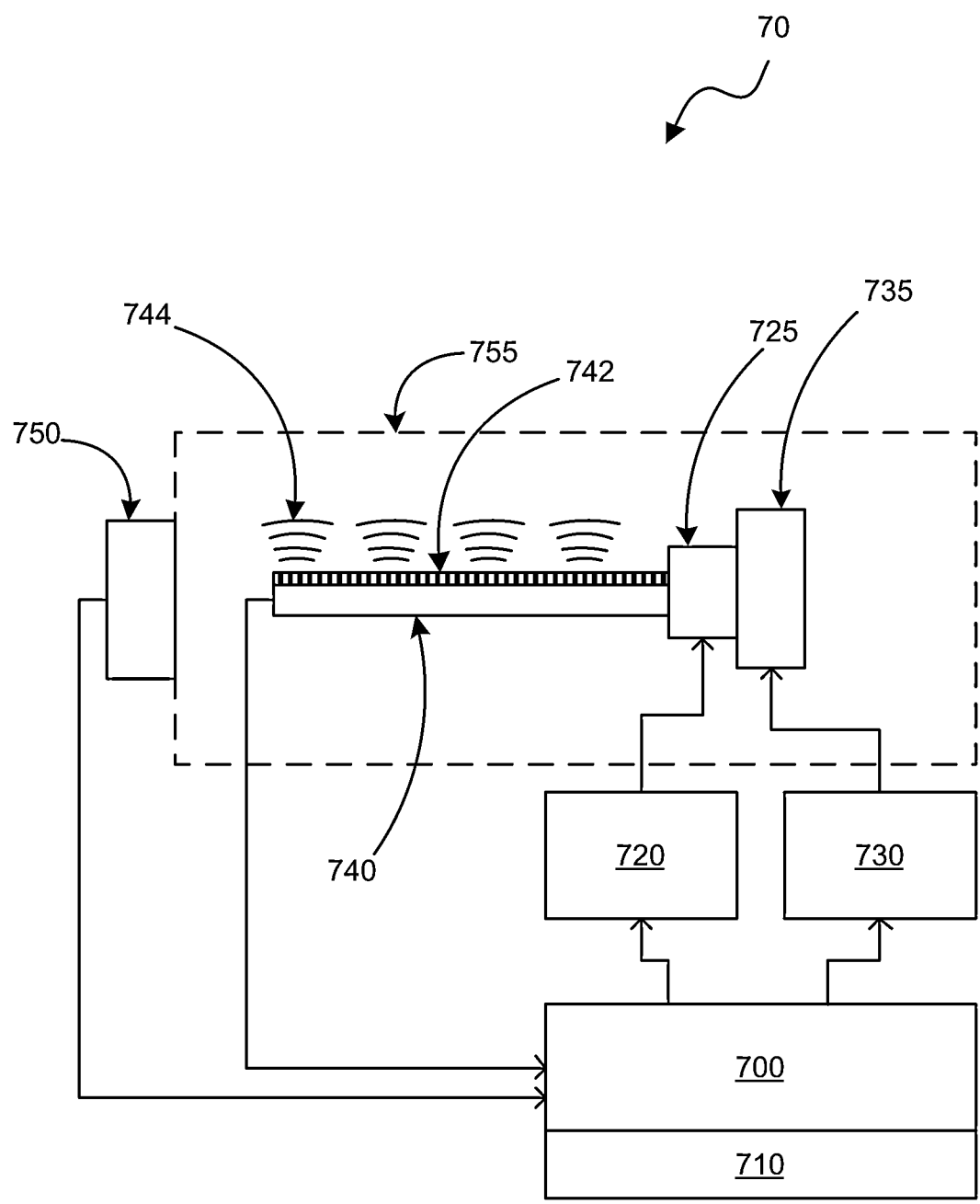
FIG. 7 illustrates an exemplary block diagram of a thermal therapy system according to one or more of the present embodiments.

FIG. 7 illustrates a block diagram of some major components of an image-guided thermal therapy system 70 consistent with the above discussion. A computer, server, processor, or other electronic processing apparatus 700 is central to monitoring and controlling the therapy procedure. The computer 700 may include or be coupled to a user interface 710 that allows operators to observe and control or have input to and derive output from the computer 700 and other elements of the system 70. It will be apparent to those skilled in the art that computer 700 may be a dedicated or general type machine, and that this computer may further include data storage and processing components, and that it may be coupled to a database, a network or other computing elements.

Computer 700 delivers signals to a motor controller 730 that controls and provides motor driving signals to a motor 735 to cause movement and rotation of the thermal therapy device 740. Such motors and controllers have been described in earlier applications by the present applicant and assignee, referenced above, which are hereby incorporated by reference.

Ultrasound therapy device 740 includes a plurality of ultrasonic transducer elements arranged in an ultrasound array 742 that is generally mounted along a long axis of the therapy device and suited for insertion into a body cavity to treat a diseased organ, e.g. trans-urethrally treating the prostate. The ultrasound elements of array 742 generate ultrasound energy 744 that is deposited into selected regions of diseased tissue.

The ultrasound array 742 is driven with electrical signals provided through electrical coupling 725, which driving signals are generated by an amplifier 720 that is controlled by computer 700.

Of course the overall arrangement and configuration of the system 70 can take on numerous forms, and some components may be further sub-divided or may be combined as deemed appropriate for a given application. The present example is being provided for the purpose of illustration.

As stated before, the patient (not shown) and the ultrasound therapy device 740 and other components are provided in a medical imaging environment 755. For example, a MRI device 750 may be used to collect thermal maps or other image data relating to the patient and the therapy. The imagery are provided to computer 700 for processing and further control of the therapy procedure. Decisions may be made by human operators or by machines, e.g. computer 700, to determine the energy levels to apply, the individual transducer controls, the mechanical rotation of the motor 735, or other alarm and control decisions.

In the present example, a processor in computer 700 executes instructions that allow performance of some or all of the steps of the methods described above. These include determination (sometimes with human or pre-determined input) of maximum temperature levels, maximum thermal doses, and other predictive calculations to conduct the present thermal therapy treatment without exceeding a safe energy or temperature limit in the patient.

The above system can be operated in a number of modes. In one mode, the system is initialized. In the initialization mode the system is not heating the target tissue. Reference images are collected and temperature maps are displayed to the operator and background noise levels are analyzed.

The system can also be operated in a "point and shoot" mode of operation. This mode provides heat build up capability at selected locations of the target tissue. This mode is off by default, but can be activated for example in testing scenarios to heat tissue along a certain direction proximal to and radially emanating from the applicator's active surface towards the treatment boundary. The applicator is not rotating about its axis in the point and shoot mode. In an example, the applicator is controllably rotated to point towards a determined angular location, then all selected transducer elements of the applicator are turned on and provided with driving signals to raise the temperature of the control point at the boundary surface to a target temperature, e.g., 55 Celsius. Individual elements can be turned on or off or have their power modulated or applied in a duty cycle if such elements' control points reach their target temperature (or are predicted to reach the target temperature) before the other elements reach theirs.

Yet another mode of operation is a heat and rotation mode, which can be the primary or main mode of operation of the therapy system during operation. In an embodiment, rotation of the therapy applicator is performed at a controllable rate of rotation about its axis. The control point for points or a given element (e.g., in a slice of the treatment volume) may be indicated at the intersection of a normal line emanating radially from the element's active surface and the target boundary in that element's slice of the treatment volume. Rotation may be initiated instantly or substantially upon commencement of the treatment procedure.

Still another mode of operation is a cool down mode. Power is secured to the elements of the therapy applicator and rotation of the applicator is halted. Temperature maps are obtained and the operator monitors the cooling of the treatment volume following treatment. Once the tissue has sufficiently cooled down, the system and the operator can stop monitoring the temperature maps in the patient. The applicator can then be removed from the patient's body or a new treatment plan can be initiated.

Figure 8:
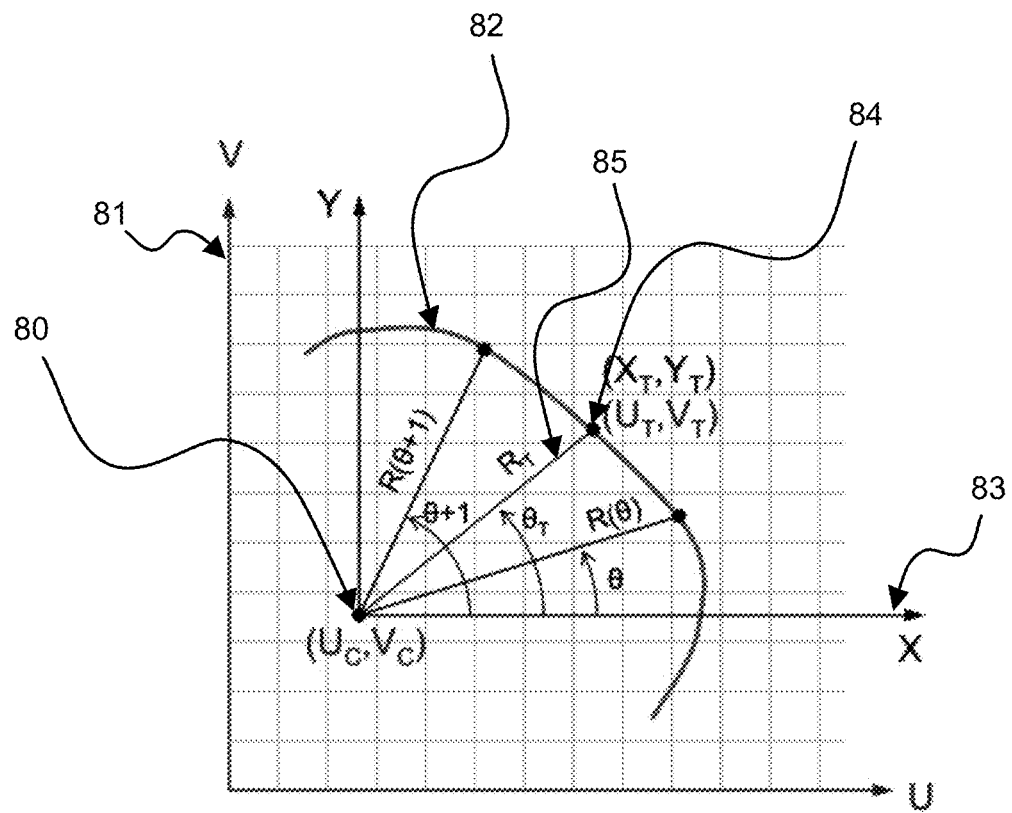
FIG. 8 illustrates a geometry that can be used in describing the conformal heating therapy within a control zone and control point(s) thereof.

The present discussion has made reference to temperature at a control point, plurality of discrete control points, or a continuous series of control points, lines, curves, surfaces or volume. FIG. 8 illustrates this notion in more detail. As discussed earlier, a treatment plan, preferably involving imaging of a patient's anatomy and disease, results in a defined target boundary 82. The target boundary 82 may be substantially conforming to a boundary of the diseased organ or a boundary of diseased tissue within the afflicted organ, or by some safety offset from the periphery of the target volume. Consider a 2D image plane in pixels (U, V) 81 having a coordinate system origin at the bottom left corner of the image. Therefore this image plane is in units of pixels. A world plane slice is represented by plane (X, Y) 83, which is measured from an origin that represents the lower left corner of the image. Therefore this world plane is in units of distance, e.g., millimeters. The target boundary 82 can be represented as polar coordinate sets having radial and angular coordinates. Of course this framework is illustrative and not limiting in the present example.

The center of the therapy applicator is at location 80, which here means that the elongated body of the therapy device runs in and out of the page normal to the slices (U, V) 81 and (X, Y) 83. In this framework, the control point in this plane is at 84 where a ray 85 intersects the target boundary surface 82. Angular positions are measured by angle theta ($\theta$) from the X axis. Interpolation can be used to obtain a more precise value for the location of the control point 84 if it lies between two adjacent units of measurement. Similarly, interpolation of the temperature at the control point is also possible for greater accuracy and smoothness during the thermal therapy procedure. If the ultrasound beam 85 is considered to have a certain width where it intersects the target boundary surface 82, multiple control points on either side of or surrounding, adjacent to or proximal to position 84 where $\theta_0 = \theta + n\Delta\theta$ and n is an integer between –N and N (including n=0).

Figure 9:
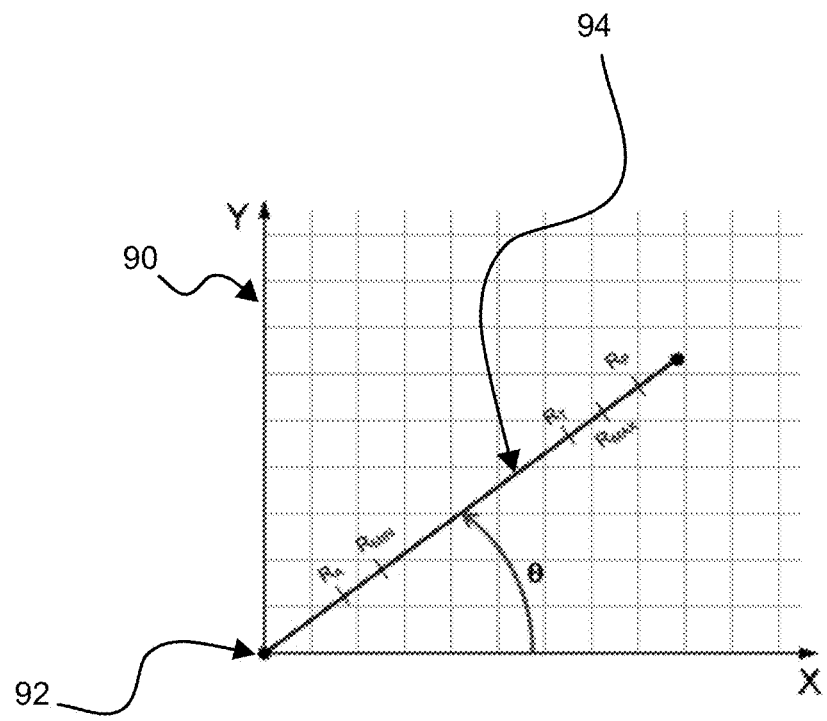
FIG. 9 illustrates key radial points used in describing the present system and process.

FIG. 9 illustrates the polar geometry which the present method and system may employ for representing temperature and other data mapped within a slice along the length of elongated applicator 206. In the (X, Y) frame 90 a center of the coordinate system 92 coincides with the center of the applicator and patient's urethra containing the applicator. The active surface or face of the applicator is directed at an angular position theta ($\theta$) at a given moment in time. A radial line 94 emanates from the active face of a transducer element in the shown slice. Distances along this line 94 can be measured relating to its origin 92. For example, the radius of the applicator device is $R_A$; the minimum radius for thermometry is $R_{MIN}$; the control boundary radius is $R_T$ at which point the control point is defined; $R_{MAX}$ represents the maximum thermometry radius and is typically between the target boundary and the edge of the prostate boundary and is usually within the limits of the prostate organ where water content enables a reliable temperature determination in MRI thermometry applications; and $R_P$ represents the radius where the prostate boundary is located.

Figure 10:
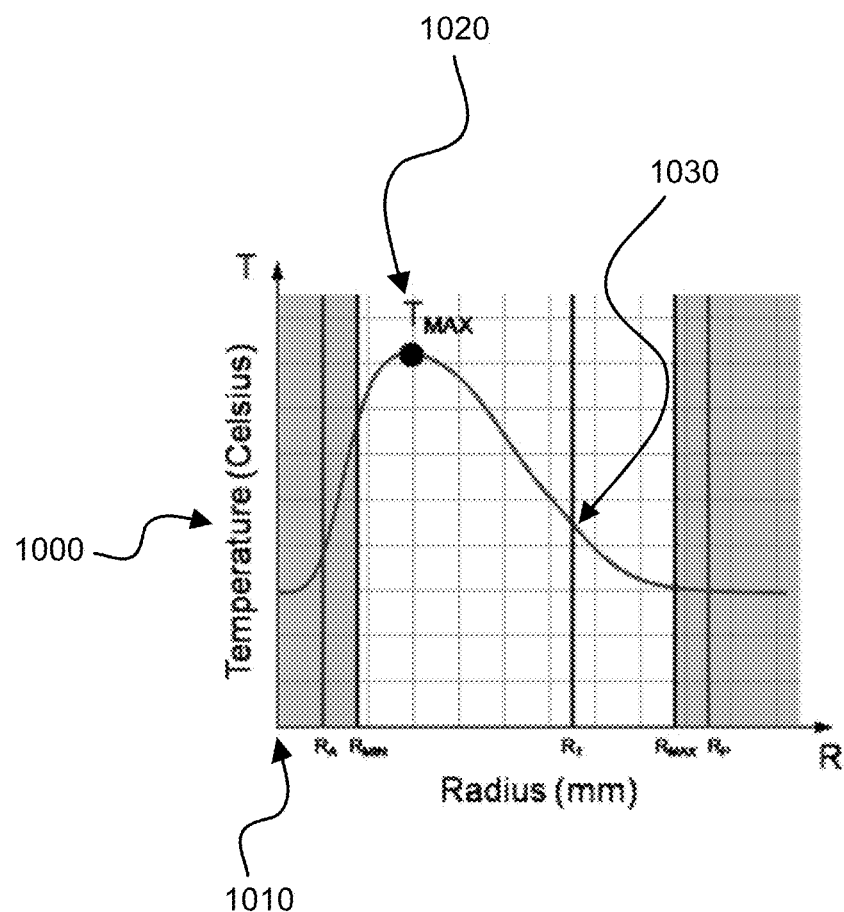
FIG. 10 illustrates a radial temperature profile from the present treatments.

FIG. 10 illustrates an exemplary temperature profile 1000 along a radius such as shown in the previous figure at a given moment in time. A temperature 1010 is defined, determined or measured at the origin of the polar coordinate system. Note that at the center near the applicator the temperature may be determined from thermocouple or other temperature sensors or thermometers, and this can be combined with or augment the imaging thermometry data described earlier. The temperature 1000 has a peak value $T_{MAX}$ 1020 at some radial distance from the applicator in this slice at this time. The temperature falls off and has another value 1030 at the control point at radius $R_T$.

Figure 11:
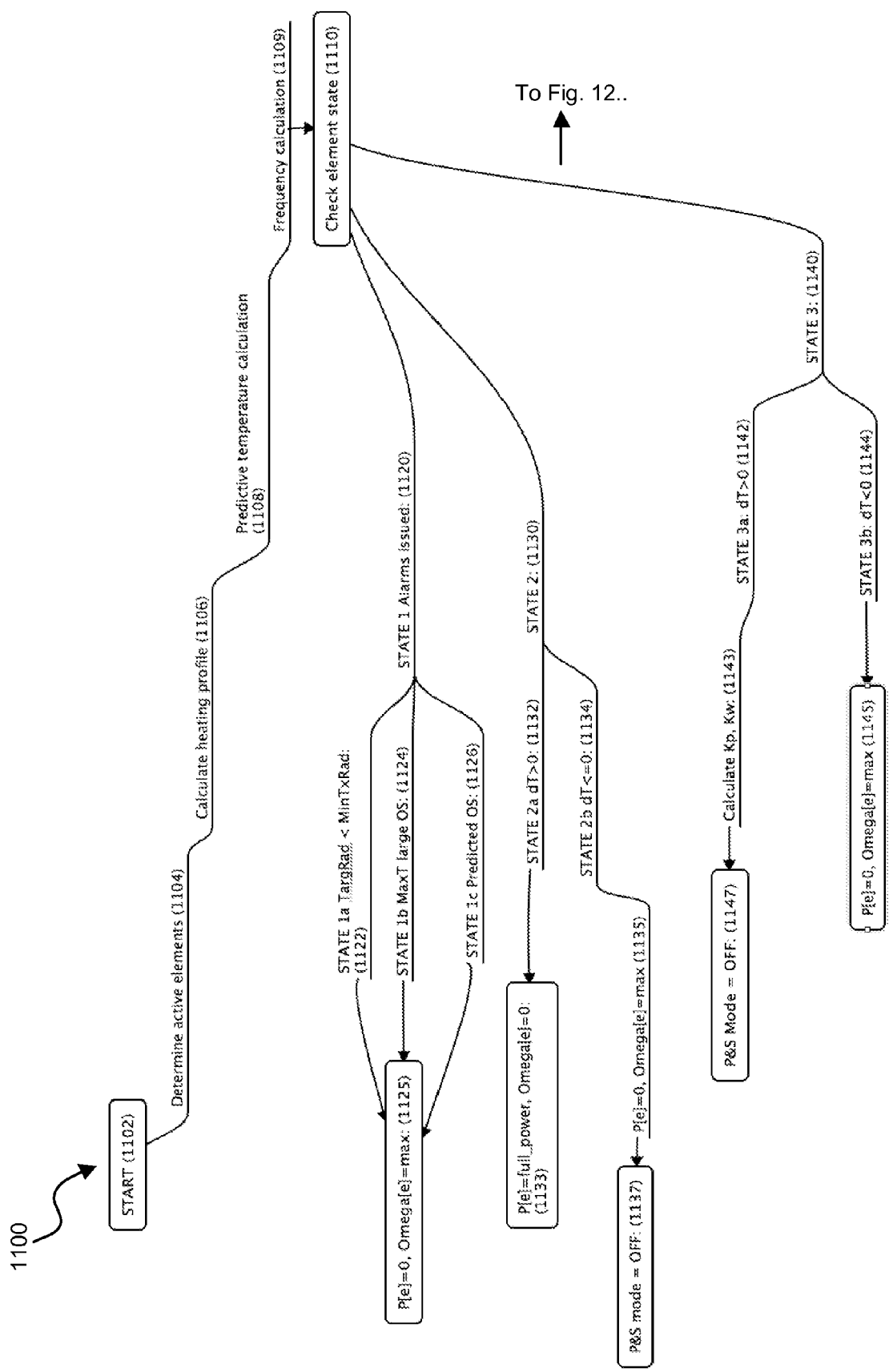
FIGS. 11 and 12 illustrate exemplary decision paths in a method for controlling a thermal therapy device that includes monitoring and time-predictive aspects from one or more control points near a target volume boundary.

FIG. 11 illustrates an exemplary sequence of steps in a thermal therapy process 1100 using the present systems and methods. The treatment commences at 1102. Individual elements of the treatment applicator device, whose point and shoot state is normally initialized to OFF, are determined as active in 1104 according to a procedure or treatment plan. A heating profile and one or more control point temperatures are calculated at 1106. Predictive temperature calculations are performed at 1108 using known data and a model for thermal performance of the system and patient's anatomy.

Figure 12:
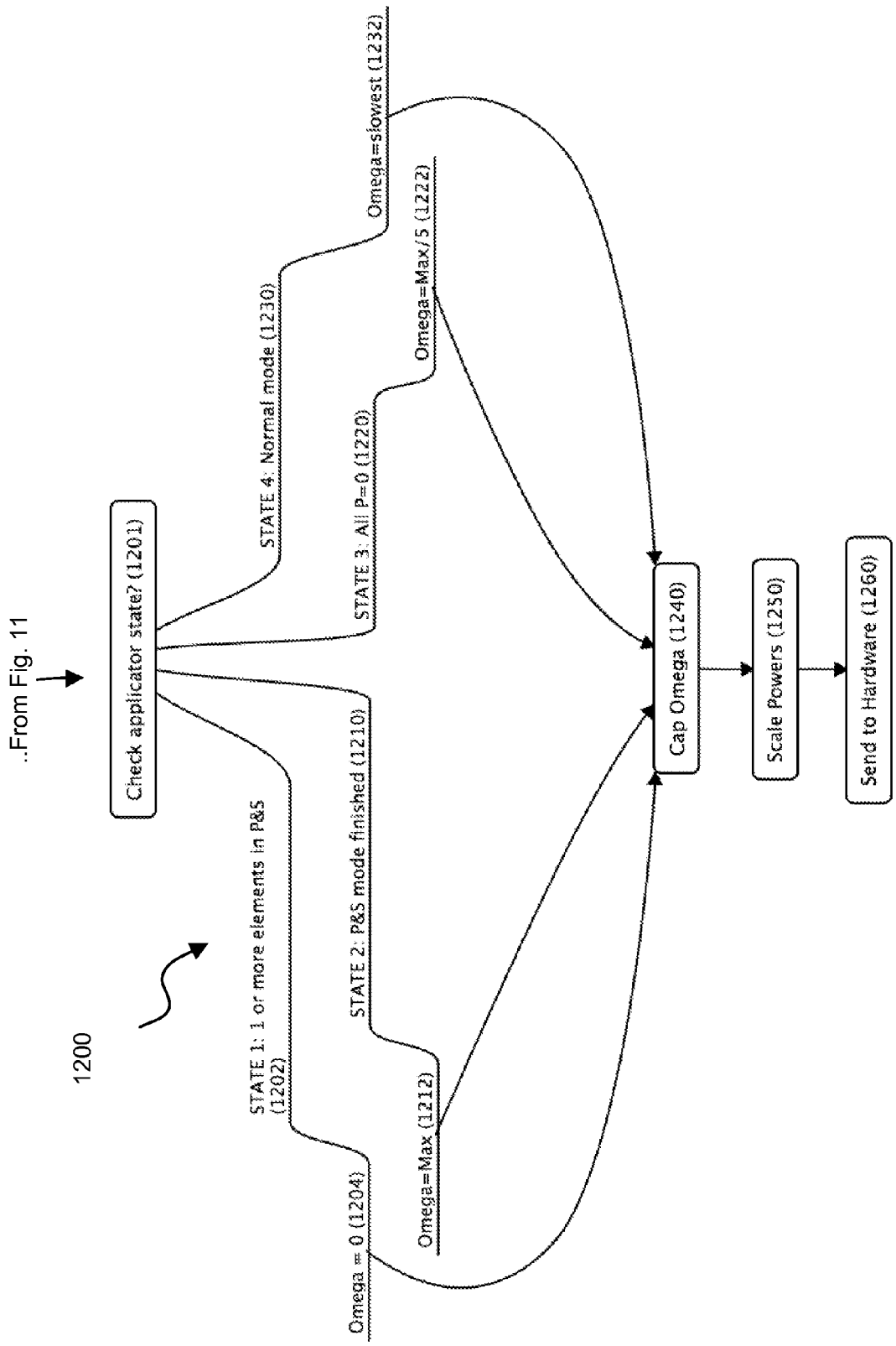

FIG. 12 illustrates a continued series of steps in providing an output control signal at 1260 to hardware implementing the present thermal therapy. Aspects used in making therapy control decisions 1100, 1200 include: predicted temperature overshoot (exceeding a desired or set goal temperature at one or more locations) (1124, 1126); a state of a therapy applicator or individual elements of the applicator (1104, 1120, 1130, 1140, etc., 1110); current device settings, speeds of rotation, power to individual elements; and alarm settings. Output control signals are sent to the treatment device hardware (1260), e.g., driving signal generators, amplifiers, motors. A maximum rotation rate may be defined (1204) for the device, which may be used to scale the power to a given element (1250) because in an embodiment of the device the elements all rotate at a common rate and therefore if one element is computed to ideally rotate at a different rate it cannot be so rotated. Instead, the power to that element may be scaled appropriately (1250) to compensate for its actual (versus its desired) rotation rate. Also, a maximum or full power to one or more elements may be defined. Therefore, a cap of either or both the rotation rate and the power of the therapy device elements can be devised and set.

Figure 13:
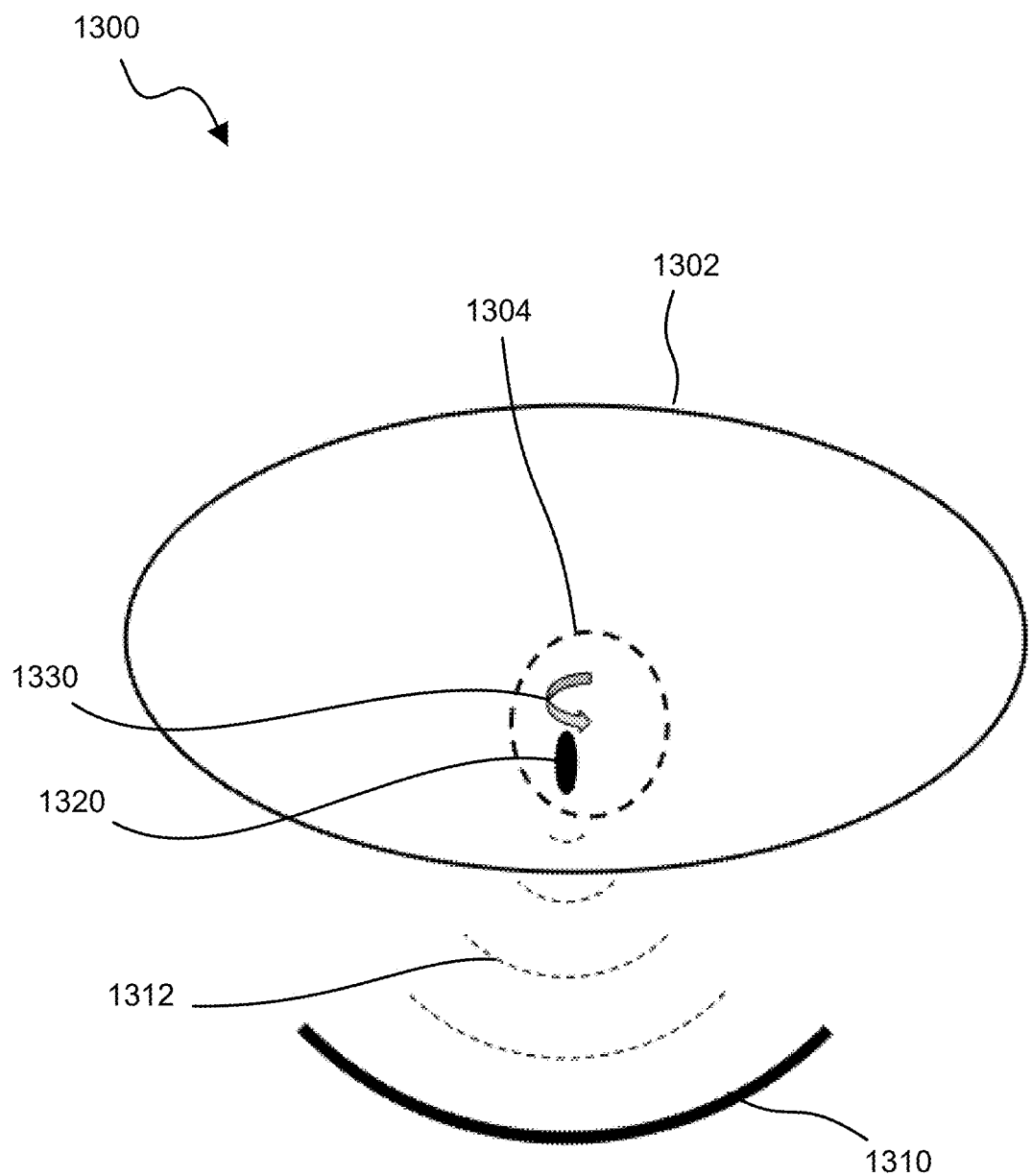
FIG. 13 illustrates a thermal therapy such as FUS or HIFU where the source of the energy is placed outside the diseased target volume.

FIG. 13 illustrates another conformal thermal therapy mechanism 1300 according to embodiments of this invention. Unlike other embodiments, here the therapy is delivered from a location outside the diseased target tissue volume rather than from within the target volume. Examples of such external thermal treatments include focused ultrasound surgery (FUS) or high intensity focused ultrasound (HIFU) and others. In the example of FIG. 13, heating ultrasound energy is created in a transducer or array of transducers 1310 that supply acoustic waves 1312 directed towards a focal spot 1320 in a target volume 1304 of a patient's body 1302. At any given time, the energy source 1310 is spatially directed either directly through moving the source 1310 or by applying phased driving signals to elements of the source 1310 so that its beam of energy 1312 is spatially moved about a treatment zone 1304. The focal spot 1320 is the primary location of heating, especially from superposition of waves and energy at this focal spot. Heat is conducted and transported outwardly from heated focal spot 1320 according to the laws of heat transfer described above, including through perfusion in the volume at and near focal spot 1320.

By scanning or translating or shifting the location of focal spot 1320 it is possible to tile or paint a thermal dose or temperature rise within the diseased target volume 1304 to treat a disease therein. A mechanism for moving or scanning the focal spot 1320 is depicted schematically by 1330 and can be any of the continuous or discrete schemes for movement of the focal spot 1320 that are known or devised in this field.

A salient point is that the heating of the tissue within target treatment volume 1304 is occurring from the inside out (from focal spot 1320 or a plurality of such focal spots, whether or not applied simultaneously). So even though the source of energy 1310 is not inside the boundary 1304, the heat affecting the treatment of the tissue in volume 1304 is effectively emanating substantially from within the volume 1304 as far as the equations of heat are concerned. Accordingly, the time-predictive methods described above apply and are applied to this scenario in some embodiments. A control point, or a plurality of control points, or a control surface or boundary may be defined at or near or corresponding to a diseased volume of tissue. Computations are performed to predict a future value of temperature or thermal dose distribution at or near such control points. The result of these computations are then used to control the spatial scan rate of the source 1310, the power and driving signals applied to the source 1310 or individual elements thereof, and so on as discussed earlier. In this way the system of 1300 can better deliver conformal thermal therapy in a diseased volume, preferably in conjunction with real time thermometry such as image guided thermal imaging in and around the diseased target volume.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure.

What is claimed is:

1. A method for treating a prostate, comprising:
   determining a target boundary defining a target treatment volume within the prostate;
   inserting a multi-element ultrasonic thermal therapy applicator at least partially within said target treatment volume;
   applying controlled driving signals to a plurality of elements of said applicator so as to controllably raise a temperature of a portion of said target treatment volume including in a region proximal to an active face of said applicator and along a direction radially emanating therefrom;
   imaging said target treatment volume using an imaging modality to determine a current temperature distribution within said target treatment volume;
   determining a future temperature distribution in a portion of said target treatment volume based at least on the current temperature distribution in and proximal to that portion using a thermal response model;
   controlling said driving signals to the plurality of elements of the applicator based at least on the determined future temperature distribution; and
   generating an alarm condition in the event that a temperature excursion is predicted to occur in said future temperature distribution according to a pre-programmed threshold for said alarm condition.

2. A system for treating a prostate, comprising:
   an ultrasonic thermal therapy applicator in the form of an elongated cylindrical applicator sized and shaped for insertion into a male patient's urethra so as to be able to reach at least partially into a prostate of said patient;
   a controllable motor and mechanical driver assembly coupled to said applicator so as to cause the elongated cylindrical applicator to rotate about an axis thereof within the patient's urethra;
   a plurality of transducer elements in said applicator, each being controllably driven by an electrical driving signal and having an active surface and capable of generating an acoustic radiation field emanating radially outwardly from its active surface into said prostate;
   a thermometry module receiving data from an imaging system and executing instructions in a processor to determine a current temperature distribution map within said prostate;
   a temperature prediction module receiving said current temperature distribution map as data, and using programmed thermal response model instructions, generating data representative of a future temperature distribution within said prostate;
   a controller receiving at least said future temperature distribution, comparing said future temperature distribution to an indicated reference temperature at least in some region within said prostate, and modifying the controllable electrical driving signals to said plurality of transducer elements in said applicator; and
   a special event module that generates an alarm condition in the event that a temperature excursion is predicted to occur in said future temperature distribution according to a pre-programmed threshold for said alarm condition.

3. The system of claim 2, said controller further controlling an electrical driving signal that controls a movement of said controllable motor so as to cause a corresponding controlling of an angular motion of said applicator within the urethra of the patient.

4. The system of claim 2, further comprising a user interface module allowing an operator to enter inputs into said system and to receive outputs from said system.

5. The system of claim 4, said user interface comprising a graphical representation of a temperature distribution within said prostate and further comprising a graphical indication of at least a portion of said target treatment volume delineated by a target boundary surrounding said portion of the target treatment volume.

6. The system of claim 2, said alarm condition being associated with an audible or visible alarm signal to an operator of the system.

7. The system of claim 2, said alarm condition causing a reduction or interruption of at least some electrical driving signals to at least some elements of said applicator.

8. The system of claim 2, said alarm condition causing a reduction or interruption of a rotation of said motor and mechanical driver assembly so as to slow down or halt a rotation of said applicator within the urethra.

9. A method for conformal thermal therapy of a diseased organ using a thermal therapy device, comprising:
   calculating a plurality of parameters in a treatment plan, including a target boundary, corresponding to conditions of a diseased organ and corresponding to therapeutic operating conditions of the therapy device;
   delivering thermal therapy to a diseased region of said diseased organ by application of a prescribed power to at least one of a plurality of ultrasound transducer elements of said therapy device;
   monitoring a temperature of said diseased organ using an imaging modality capable of mapping acquired images to corresponding present temperature maps within said diseased organ;
   executing, in a processor, programmed steps representing a thermal model, taking as input at least said present temperature maps and outputting at least a future temperature distribution predicted by said thermal model;
   generating control signals, at least in part based on said future temperature distribution predicted by said thermal model; and controlling operation of said therapy device at least in part based on said generated control signals; and generating an alarm condition in the event that a temperature excursion is predicted to occur in said future temperature distribution according to a pre-programmed threshold for said alarm condition.

10. The method of claim 9, monitoring said temperature in said diseased organ comprises monitoring a temperature at a control point defined by intersection of a direction of a beam of ultrasound emitted from said therapy device and said target boundary.

11. The method of claim 9, monitoring said temperature in said diseased organ comprises monitoring temperatures at a plurality of control points spatially defined along a radial direction of a beam of ultrasound energy emitted from said therapy device.

12. The method of claim 9, monitoring said temperature in said diseased organ comprises monitoring temperatures at a plurality of control points spatially defined along at least a portion of said target boundary.

13. The method of claim 9, controlling said operation of the therapy device comprising controlling a movement of said therapy device so as to cause a corresponding translation of a heating zone of said thermal therapy.

14. The method of claim 9, controlling said operation of the therapy device comprising controlling phasing of a multi-element phased array in said therapy device so as to cause a corresponding shift in a location of a focal spot of said therapy device.

15. The method of claim 9, further comprising placing at least a portion of an unfocused ultrasound therapy device into an interior volume of said target boundary and emitting an unfocused acoustic field from an active surface of said therapy device.

16. The method of claim 15, further comprising rotating said unfocused ultrasound therapy device about an axis thereof to conformally treat an extended volume of tissue within said target volume.

17. The method of claim 9, further comprising placing a focused ultrasound therapy device outside said target boundary and directing a focus of said focused ultrasound therapy device into an interior volume of said target boundary and delivering a focused acoustic field from an active surface of said focused therapy device.

18. The method of claim 17, further comprising controlling respective phases of a plurality of elements of a focused multi-element phased array to conformally treat an extended volume of tissue within said target volume.

* * * * *